United States Patent

Kashihara et al.

Patent Number: 5,929,257
Date of Patent: Jul. 27, 1999

[54] PROCESS FOR PRODUCING TRIOXANE

[75] Inventors: Osamu Kashihara; Minoru Akiyama, both of Fuji, Japan

[73] Assignee: Polyplastics Co., Ltd., Japan

[21] Appl. No.: 08/930,180

[22] PCT Filed: Apr. 22, 1996

[86] PCT No.: PCT/JP96/01086

§ 371 Date: Oct. 20, 1997

§ 102(e) Date: Oct. 20, 1997

[87] PCT Pub. No.: WO96/33188

PCT Pub. Date: Oct. 24, 1996

[30] Foreign Application Priority Data

Apr. 21, 1995 [JP] Japan ............................ 7-96413

[51] Int. Cl.⁶ .............................................. C07D 323/06
[52] U.S. Cl. ........................................................ 549/368
[58] Field of Search ............................................. 549/368

[56] References Cited

FOREIGN PATENT DOCUMENTS

| | | |
|---|---|---|
| B-41-6344 | 5/1962 | Japan . |
| A-58-203985 | 11/1983 | Japan . |
| A-63-264579 | 11/1988 | Japan . |
| A-4-49250 | 2/1992 | Japan . |
| A-6-73046 | 3/1994 | Japan . |

OTHER PUBLICATIONS

Liu et al, Study of Ion–Exchange,etc., Lizi Jiaohuan Yu Xifu, 4(4), pp. 298–304, 1988.

Kirk–Othmer, Encyclopedia of Chemical Technology (4th. Ed.), vol. 14, pp. 737–739,744–745, 760, 761, 764, 766–769, 773, 774 and 778, 1995.

*Primary Examiner*—Bernard Dentz
*Attorney, Agent, or Firm*—Nixon & Vanderhye P.C.

[57] ABSTRACT

To provide a practical and economical process for producing trioxane from an aqueous formaldehyde solution in the presence of a solid acid catalyst, which permits a stable operation for a long period of time.

A process for producing trioxane from an aqueous formaldehyde solution by using a production apparatus comprising two functional steps, i.e. the first functional step of conducting mainly the removal of metallic impurities from the aqueous formaldehyde solution with a substance having an ion-exchanging function and the second functional step of conducting mainly the synthesis of trioxane from the aqueous formaldehyde solution, from which metallic impurities have been removed, with a solid acid catalyst.

11 Claims, 1 Drawing Sheet

PROCESS FOR PRODUCING TRIOXANE

This application is a 371 of PCT/JP96/01086 filed Apr. 22, 1996.

FIELD OF THE INVENTION

The present invention relates to a practical and economical process for producing trioxane useful as the raw material of polyoxymethylene from an aqueous formaldehyde solution.

BACKGROUND OF THE INVENTION

Trioxane which is a cyclic trimer of formaldehyde is generally prepared by heating an aqueous formaldehyde solution in the presence of an acid catalyst. With respect to this preparation, it is known that the equilibrium concentration of trioxane in the liquid phase is as low as about 2 to 4% by weight to give a large amount of unreacted formaldehyde even when the concentration of the starting aqueous formaldehyde solution is 30 to 70% by weight. Accordingly, it is necessary for the recovery of pure trioxane that the reaction mixture containing trioxane must be first freed from the acid catalyst, followed by the separation of trioxane of pure state from formaldehyde, water and so on.

As a specific process for producing trioxane, JP-B-41-6344 discloses a process which comprises reacting a 30 to 70% (by weight) aqueous formaldehyde solution under heating in the presence of a liquid acid catalyst such as sulfuric acid, distilling the resulting reaction mixture to separate a distillate comprising trioxane, formaldehyde and water from the liquid acid catalyst, and recovering pure trioxane from the distillate by solvent extraction or the like.

However, such a process using a liquid catalyst such as sulfuric acid as the catalyst for the synthesis of trioxane has a problem that the separation of the trioxane-containing component from the catalyst involves an operation necessitating much energy, for example, distillation.

On the contrary, processes using various solid acids, for example, organic solid acids such as a strongly acidic cation-exchange resin or inorganic solid acids such as zeolite have been proposed as processes permitting easy removal of the catalyst from the trioxane-containing reaction mixture to thereby cut down the energy necessary therefor. Further, there have also been proposed economical processes of directly recovering pure trioxane by solvent extraction from the solution obtained by separating the solid acid catalyst from the reaction mixture containing trioxane (JP-A-4-49250 and JP-A-6-73046).

These processes have an advantage in that substantially no energy is necessary for the removal of the catalyst from the reaction mixture.

In the follow-up made by the inventors of the present invention, however, long-term stable operation was substantially impossible when the above process for producing trioxane with a solid acid catalyst was merely applied to a conventional actual plant.

As described above, the equilibrium concentration of trioxane in preparing trioxane from an aqueous formaldehyde solution in the presence of an acid catalyst is low, so that a large amount of unreacted formaldehyde remains in the resulting aqueous solution. In order to produce a desired amount of trioxane, therefore, a large amount of an aqueous formaldehyde solution must be brought into contact with a solid acid catalyst and a large amount of an aqueous solution of unreacted formaldehyde must be recovered and re-used as the starting aqueous formaldehyde solution for the synthesis of trioxane. However, the above processes have a problem that the activity of a solid acid catalyst rapidly lowers in a short period of time and the rate of formation of trioxane lowers with this lowering in the activity, which makes it difficult to produce a desired amount of trioxane constantly. Further, the processes have another problem that increase in pressure loss or channelling occurs in the reactor containing a solid acid catalyst in a short period of time, which makes it difficult to attain the feeding of an aqueous formaldehyde solution at a constant flow rate or the production of trioxane in a constant amount.

SUMMARY OF THE INVENTION

The present invention is embodied a process for producing trioxane from an aqueous formaldehyde solution, characterized by using a production apparatus comprising two functional steps, i.e., the first functional step of conducting mainly the removal of metallic impurities from the aqueous formaldehyde solution with a substance having an ion-exchanging function and the second functional step of conducting mainly the synthesis of trioxane from the aqueous formaldehyde solution, from which metallic impurities have been removed, with a solid acid catalyst. Namely, it is a process that first metal impurities are removed from aqueous formaldehyde solution and next trioxane is synthesized.

Preferably, the solid acid catalyst in the second functional step is a strongly acidic cation-exchange resin.

Preferably, the second functional step is conducted in one column filled with the solid acid catalyst.

Preferably, the synthesis of trioxane in the second functional step is conducted in an ascending stream of the aqueous formaldehyde solution.

Preferably, the substance having an ion-exchanging function in the first functional step is a cation-exchange resin.

Preferably, the first functional step is conducted in two or more columns arranged in parallel.

Preferably, the columns arranged in parallel in the first functional step are alternately used for removing the metallic impurities and for regenerating the columns.

Preferably, the removal of the metallic impurities in the first functional step is conducted in a descending stream of the aqueous formaldehyde solution.

The present invention will now be described in detail.

BRIEF DESCRIPTION OF THE ACCOMPANYING DRAWING

The accompanying drawing FIGURE shows schematically an apparatus for the continuous production of trioxane which was employed in the Example below.

DETAILED DESCRIPTION OF THE INVENTION

Figure 1:
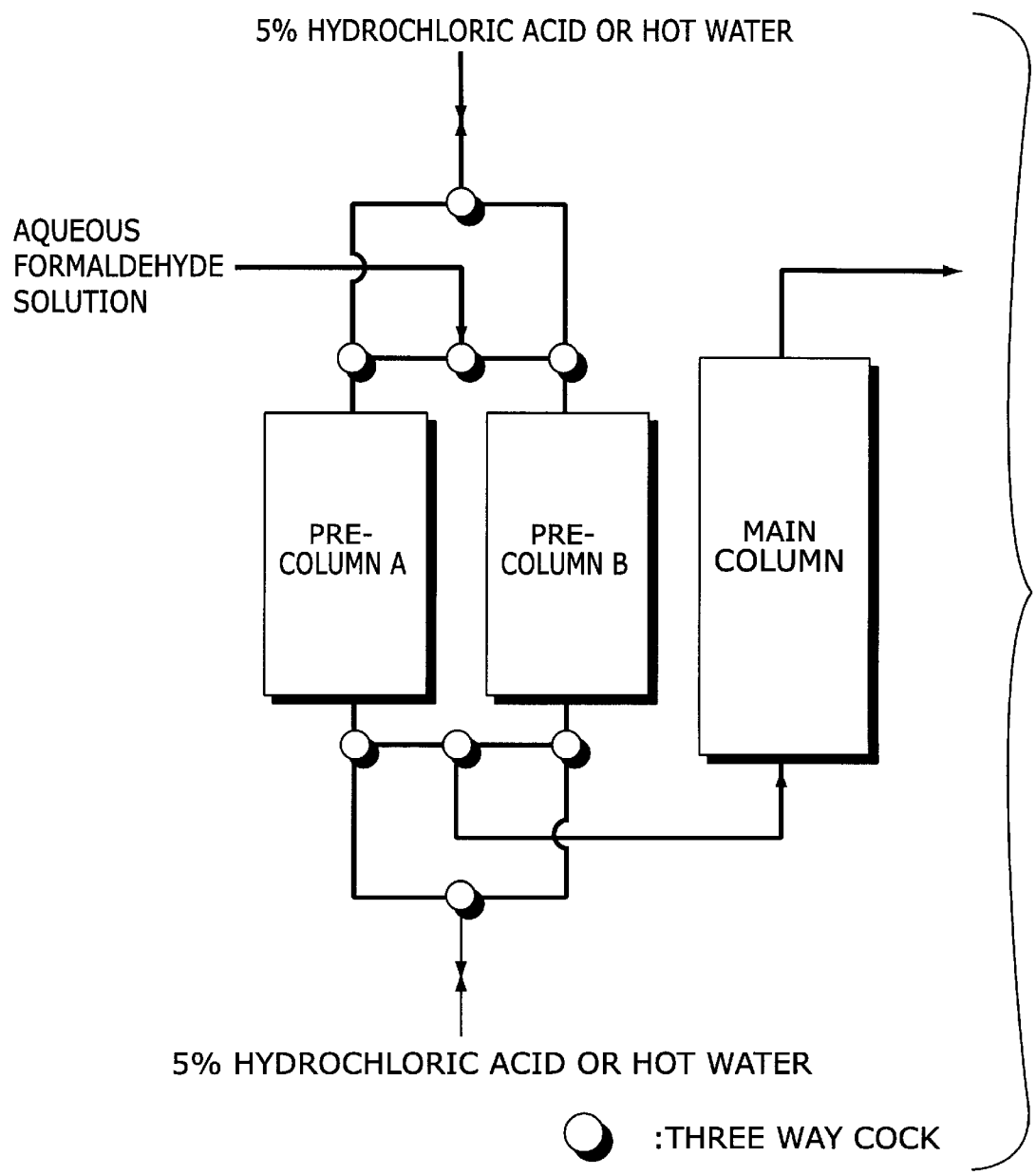

The present invention is based on the discovery that several of ppb to tens of ppm of metal ions are contained in the aqueous formaldehyde solution used in the production of trioxane in a practical plant. It has been found, therefore, that the catalytic activity of the solid acid is lowered by the adsorption of such metal ions on the solid acid to adversely affect the synthesis of trioxane significantly.

There specifically owing to the low equilibrium concentration of trioxane in preparing trioxane from an aqueous formaldehyde solution in the presence of an acid catalyst, a large amount of an aqueous formaldehyde solution must be used for the reaction and brought into contact with a solid acid catalyst, and a large amount of an aqueous solution of unreacted formaldehyde must be recovered and re-used as the starting aqueous formaldehyde solution for the synthesis of trioxane. Meanwhile, metal ions are eluted from apparatus, pipe and so on in the step of producing a starting aqueous formaldehyde solution, the step of recovering an aqueous solution of unreacted formaldehyde, and the steps of storage, transfer and concentration of these solutions.

On the other hand, the solid acid used as catalyst is a substance having an ion-exchanging function. This substance adsorbs metal ions at its acidic sites through ion exchange to result in deactivation and owing to this deactivation, the function of the substance as the acid catalyst for the synthesis of trioxane is lowered to fail in long-term use of the substance.

It was surprising that the presence of a trace amount of metal ions in the aqueous formaldehyde solution becomes a fatal factor hindering stable operation in the practical production of trioxane.

Additionally, further studies made by the inventors of the present invention revealed that the generation of paraform which is a solid oligomer of formaldehyde becomes easier with an increase in the concentration of a starting aqueous formaldehyde solution and that when paraform is present in the aqueous formaldehyde solution, it accumulates as a sediment in the reactor filled with a solid acid catalyst and this accumulation causes increase in pressure loss, inconstant flowing, channelling and so on to hinder long-term stable operation.

The present invention has been accomplished as a result of intensive studies made on the basis of the above elucidation of the causes and the findings for the purpose of finding a solution to the problems, and is, as described above, characterized in that the production of trioxane from an aqueous formaldehyde solution is conducted through two functional steps, i.e., the first functional step of conducting mainly the removal of metallic impurities from the aqueous formaldehyde solution with a substance having an ion-exchanging function and the second functional step of conducting mainly the synthesis of trioxane from the aqueous formaldehyde solution, from which metallic impurities have been removed, with a solid acid catalyst. In other words, the present invention is characterized in that in order to attain long-term stable operation, the production of trioxane with a solid acid catalyst from an aqueous formaldehyde solution is divided into two functions, i.e., the function of dealing with the factors hindering stable operation and that of attaining the reaction.

The aqueous formaldehyde solution to be used in the production of trioxane according to the present invention includes aqueous formaldehyde solutions prepared by conventional processes, those prepared by purification, concentration or dilution of these solutions, and a recovered aqueous solution of unreacted formaldehyde. Alternatively, a mixture of two or more of them may be used. Although the concentration of the aqueous formaldehyde solution to be used is not particularly limited, it is generally 30 to 80% by weight, preferably 50 to 70% by weight.

In the present invention, such an aqueous formaldehyde solution is subjected to the first functional step wherein the removal of metallic impurities from the aqueous formaldehyde solution is mainly conducted with a substance having an ion- exchanging function.

The substance to be used for the removal of metallic impurities in the first step is not particularly limited but may be any one having such a function. For example, many of the substances which will be described as examples of the solid acid to be used in the second functional step can be used. In particular, cation-exchange resins are preferable.

In the first functional step, the performance of a substance having an ion-exchanging function is deteriorated by adsorption of metallic impurities thereon with the lapse of time to result in unavoidable regeneration. Further, paraform resides and accumulates in the apparatus to cause operational troubles. In order to deal with such circumstances to enable continuous operation, it is preferable in the present invention that the first functional step be constituted of two or more columns arranged in parallel. Each column is filled with a substance having an ion-exchanging function. When the first functional step is constituted of two or more columns, at least one of the columns can be used for the pretreatment of an aqueous formaldehyde solution, i.e., the removal of metal ions therefrom, while the other which has been lowered in ion-exchanging function by adsorption of metal ions can be used for regeneration. Thus, the columns can be used alternately or successively for the removal of metal ions and for regeneration to permit continuous operation for a long period of time. Although the number of columns to be specifically employed in practice is determined by considering the components of a starting aqueous formaldehyde solution, economical efficiency, operability and so on, the use of two columns is generally preferable and can give enough effects. The switch from the removal of metal ions from the aqueous formaldehyde solution to regeneration and vice versa is preferably conducted once per day to once per two weeks, though the frequency of the switch is determined by considering the content of metallic impurities in the starting aqueous formaldehyde solution, residence time and easiness of operation.

It is preferable that the first functional step according to the present invention be conducted in a descending stream of the aqueous formaldehyde solution. By this preferable embodiment, the rate of adsorption of metals and the function as a filter against the paraform contained in the starting aqueous formaldehyde solution are improved as compared with the case wherein the first functional step is conducted in an ascending stream thereof. The metal ions adsorbed in this step are removed by regeneration treatment using hydrochloric acid or the like, while the paraform is effectively discharged out of the system by back wash development with an ascending stream.

The residence time in the first step may be one enough to adsorb and remove the metallic impurities contained mainly in the starting aqueous formaldehyde solution. For example, when a strongly acidic cation-exchange resin is used, enough effects can be generally attained by the residence for 1 to 5 minutes, though the residence time varies depending on operating conditions and so on. Too long a residence time will give an increased amount of formic acid as a by-product, which will have an adverse effect on the synthesis of trioxane in the subsequent second functional step.

The linear velocity of the starting aqueous formaldehyde solution in the first functional step is preferably 5 to 50 m/h, though it varies depending on the substance having an ion-exchanging function to be used. When the linear velocity is less than 5 m/h, the sectional area of column of the apparatus will be large for the capacity thereof, so that channelling will occur to fail in obtaining the expected results. On the contrary, when the linear velocity exceeds 50 m/h, the pressure loss will increase, so that it will be difficult to keep the flow rate constant.

Then, the aqueous formaldehyde solution from which mainly metal ions have been removed in the first functional step is subjected to the second functional step wherein the synthesis of trioxane is conducted with a solid acid catalyst.

The solid acid to be used in this step may be any of organic and inorganic solid acids. Examples of the organic solid acids include ion-exchange resins having sulfonic and fluoroalkanesulfonic groups, while those of the inorganic solid acids include acid clay, silica, alumina; inorganic matter-oxide composites such as silica-alumina, alumina-boria and zeolite; and solid carriers impregnated with sulfuric acid, phosphoric acid, boric acid and so on. Among these solid acids, ion-exchange resins which are organic solid acids are preferable, strongly acidic cation-exchange resins being particularly preferable. Since a solid acid is used in an aqueous formaldehyde solution in this step, it is preferable to a Brønsted acid which can keep its activity as an acid even in water and whose acid groups are not dissolved in water.

Although the constitution of the apparatus used for the second functional step is not particularly limited, it is preferable from the standpoint of the balance between synthesis efficiency of trioxane and construction cost that the apparatus be constituted of one column filled with a solid acid.

Further, it is preferable that the second functional step, i.e., the synthesis of trioxane, be conducted in an ascending stream of the starting aqueous formaldehyde solution. By employing this preferable embodiment, the troubles caused by the paraform brought into the apparatus by some rare accident or formed therein can be prevented and the paraform can be easily effused out of the column.

Although the operation conditions of the second functional step or the rate of formation of trioxane is not particularly limited, it is preferable for practical and economical production of trioxane that the reaction be conducted under such conditions as to enhance the trioxane concentration to a level substantially equilibrating with the concentration of the fed aqueous formaldehyde solution. Although the residence time necessary for satisfying the conditions varies depending on the kind of the solid acid to be used, reaction temperature or the like, it is generally 5 to 25 minutes when the operation is conducted at a reaction temperature of about 80 to 110° C. with a strongly acidic cation-exchange resin. Since the reaction through which trioxane is produced from an aqueous formaldehyde solution is an equilibrium reaction, the employment of a residence time longer than that necessary for reaching the equilibrium reaction brings about an increase in the amount of by-products such as formic acid, so that attention must be paid to the selection of the residence time. Specifically, the preferable residence time can be easily determined by simple experiments with a specific solid acid under specific reaction conditions. The amount of the solid acid to be used can be determined based on the residence time thus determined.

Although the linear velocity of the second functional step also varies depending on the kind of the solid acid to be used, it is preferably 3 to 15 m/h for fluidizing the solid acid in the column to thereby facilitate the effusion of paraform and for dispensing with a larger developing cabinet for the solid acid.

Specific examples of the type of the apparatus to be used in the above first and second functional steps include packed bed type, tubular type, basket type, fluidized bed type, plate column type and so on, though the examples are not limited to these types.

Further, the conditions of apparatus and operating conditions may be selected on the basis of the above requirements by considering the properties (formaldehyde concentration, metallic impurity content and content of suspended paraform) of the starting aqueous formaldehyde solution and the throughput thereof, the kind and amount of the solid acid to be used, the rate of adsorption of metals on solid acid, and the rate of formation of trioxane with a solid acid catalyst.

In the process for producing trioxane according to the present invention, it is generally preferable that no substance known as an inhibitor against the formation of paraform be added. The addition of such a substance is problematic in that the separation of the substance from the reaction system is troublesome and that the substance accumulates in the system to hinder not only the generation of paraform but also the formation of trioxane.

The reaction product obtained by the above process for producing trioxane according to the present invention is a mixture comprising not only trioxane but also a large amount of formaldehyde, water and a small amount of impurities. Pure trioxane can be recovered from the reaction product by known processes. In particular, it is preferable to employ a process of extracting the reaction product with a high-boiling solvent and then recovering trioxane from the extract by distillation.

On the other hand, a large amount of unreacted formaldehyde is recovered as an aqueous solution and, if necessary, subjected to concentration or other treatment; and thereafter it is generally re-used for the synthesis of trioxane.

EXAMPLE

The present invention will now be specifically explained by referring to the following Example, though it is not limited by the Example.

The apparatus, starting aqueous formaldehyde solution, operating conditions and evaluation items employed in the following Example, Comparative Example and Referential Example are as follows:

(1) apparatus first functional step: heat-insulating jacketed column having an inner diameter of 1 cm and a height of 150 cm, which is filled with 300 cc of a strongly acidic cation-exchange resin, DIAION PK216 (a product of Mitsubishi Chemical Corp.) (hereinafter referred to as "pre-column")

second functional step: heat insulating jacketed column having an diameter of 2 cm and a height of 200 cm, which is filled with 1200 cc of a strongly acidic cation-exchange resin, DIAION PK216 (a product of Mitsubishi Chemical Corp.) as a solid acid catalyst. (hereinafter referred to as "main column")

(2) aqueous formaldehyde solution

| formaldehyde concentration | 60% by weight |
|---|---|
| metallic contaminants | |
| iron ion concn. | 2.5 ppm |
| chroinium ion concn. | 1.0 ppm |
| nickel ion conch. | 0.5 ppm |

(3) operating conditions

| flow rate of aqueous formaldehyde solution (preset) | 6000 cm$^3$/h |
|---|---|
| linear velocity of pre-column | 20 m/h |

-continued

| linear velocity of main coulmn | 5 m/h |
| temp. (of both columns) | 100° C. |

(4) evaluation items
① concentrations of trioxane and metal ions in the solution discharged from the apparatus,
② real flow rate of aqueous formaldehyde solution,
③ generation and accumulation of paraform (as determined with the naked eye)

Comparative Example 1

The synthesis of trioxane was conducted in an apparatus obtained by removing the pre-columns for the first functional step from the apparatus for continuous production of trioxane shown in FIG. 1, i.e., by the use of only the main column for the second functional step. Experiments were made with respect to both the case using an ascending stream of the aqueous formaldehyde solution and the case using a descending stream thereof. The results are given in Table 1.

In any of the cases, there were observed a lowering in catalytic activity caused by the adsorption of metal ions contained in the aqueous formaldehyde solution on the surface of the solid acid and a lowering in conversion into trioxane (i.e., trioxane concentration) caused by the above lowering. In the operation using the descending stream, there was observed a lowering in flow rate caused by the accumulation of paraform on the surface of the solid acid, while in the operation using the ascending stream, there was not observed any lowering therein over a long time.

These relonts suggests that in order to attain long-term stable operation, it is necessary to remove metal ions prior to the synthesis of trioxane, and it is preferable to conduct the synthesis of trioxane in an ascending stream of the aqueous formaldehyde solution.

Referential Example 1

In order to determine the removal efficiency against metal ions contained in the aqueous formaldehyde solution, the aqueous formaldehyde solution was passed through only the pre-column corresponding to the first functional step. Experiments were made with respect to both the case using an ascending stream of the aqueous formaldehyde solution and the case using a descending stream thereof. The results are given in Table 2.

It was recognized that the operation using the descending stream is superior to that using the ascending stream in respect of the removal efficiency against metal ions.

When the operation using the descending stream was conducted for a long time, there was observed a lowering in flow rate caused by the accumulation of paraform on the surface of the packing material. Therefore, the passing of the aqueous formaldehyde solution through the column was stopped and hot water of 100° C. was passed through the resulting column as an ascending stream to discharge and remove the paraform. Thereafter, an aqueous formaldehyde solution was passed through the column again. Thus, the flow rate was restored to the original state.

From these results, there was obtained a knowledge that it is rational in order to overcome the problematic lowering in flow rate while keeping the removal efficiency against the metal ions at a high level that the first functional step is constituted of at least two columns and they are used alternately and repeatedly for the removal of metal ions and for regeneration.

Example 1

Two pre-columns (A, B) for the first functional step of conducting the pretreatment of the aqueous formaldehyde solution and one main column for the second functional step of conducting the synthesis of trioxane were connected as shown in FIG. 1, and the aqueous formaldehyde solution was passed through the resulting system to conduct the synthesis of trioxane. The pre-columns were switched at regular time intervals and alternately used. The pre-column used for the pretreatment of the aqueous formaldehyde solution for a certain period of time was subjected to the regeneration of the ion exchange resin with 5% hydrochloric acid and the removal of paraform by extraction with an ascending stream of hot water, and thus the system was continuously operated. The results are given in Table 3.

Further, similar tests were conducted by the use of the system shown in FIG. 1 also with respect to the case wherein the passing through the pre-column was conducted as an ascending stream and the case wherein the passing through the main column was conducted as a descending stream. In any of the both cases, the effects due to the provision of the pre-column were remarkable to permit stable operation for a time far longer than that of the case using only the main column, though the effects were inferior to those obtained in the above Example.

TABLE 1

Experiment on synthesis of trioxane (main column)

| | | Hours (h) | 10 | 100 | 200 | 300 | 400 | 500 | 600 | 700 |
|---|---|---|---|---|---|---|---|---|---|---|
| (a) Ascending stream | reactant solution | trioxane (wt %) | 3.2 | 3.0 | 2.8 | 2.6 | 2.4 | 2.2 | 2.0 | 1.8 |
| | | Fe (ppm) | 0 | 0 | 0 | 0 | 0 | 0.1 | 0.2 | 0.3 |
| | | Cr (ppm) | 0 | 0 | 0 | 0 | 0 | 0 | 0.1 | 9.1 |
| | | Ni (ppm) | 0 | 0 | 0 | 0 | 0 | 0 | 0 | 0.1 |
| | flow rate (m³/h) | | 6000 | 6000 | 6000 | 6000 | 6000 | 6000 | 6000 | 6000 |
| | presence of paraform (as determined with the naked eye) | | — | — | float | float | float | float | float | float |
| (b) Descending stream | reactant solution | trioxane (wt %) | 3.2 | 3.0 | 2.8 | 2.6 | 2.4 | | | |
| | | Fe (ppm) | 0 | 0 | 0 | 0 | 0 | | | |
| | | Cr (ppm) | 0 | 0 | 0 | 0 | 0 | | | |
| | | Ni (ppm) | 0 | 0 | 0 | 0 | 0 | | | |
| | flow rate (m³/h) | | 6000 | 6000 | 5700 | 5000 | 1000 | discontinued | | |
| | presence of paraform | | — | — | accumu- | accumu- | accumu- | | | |

TABLE 1-continued

Experiment on synthesis of trioxane (main column)

| Hours (h) | 10 | 100 | 200 | 300 | 400 | 500 | 600 | 700 |
|---|---|---|---|---|---|---|---|---|
| (as determined with the naked eye) | | | lation | lation | lation | | | |

TABLE 2

Test on the removal of metal ions (pre-column)

| | | | Hours (h) 10 | 50 | 100 | 150 | 200 | 250 | 300 |
|---|---|---|---|---|---|---|---|---|---|
| Ascending stream | reactant solution | Fe (ppm) | 0.5 | 0.5 | 0.6 | 0.7 | 0.7 | 1.0 | 1.5 |
| | | Cr (ppm) | 0.2 | 0.2 | 0.2 | 0.2 | 0.3 | 0.5 | 0.7 |
| | | Ni (ppm) | 0.1 | 0.1 | 0.1 | 0.1 | 0.2 | 0.3 | 0.4 |
| | flow rate (cm³/h) | | 6000 | 6000 | 6000 | 6000 | 6000 | 6000 | 6000 |
| | presence of paraform (as determined with the naked eye) | | — | — | — | — | float | float | float |
| Descending stream | reactant solution | Fe (ppm) | 0 | 0 | 0 | 0 | 0 | 0 | 0 |
| | | Cr (ppm) | 0 | 0 | 0 | 0 | 0 | 0 | 0 |
| | | Ni (ppm) | 0 | 0 | 0 | 0 | 0 | 0 | 0 |
| | flow rate (cm³/h) | | 6000 | 6000 | 6000 | 6000 | 5500 | 3000 | 1000 |
| | presence of paraform (as determined with the naked eye) | | — | — | — | — | accumulation | accumulation | accumulation |

TABLE 3

Test on continuous production of trioxane

| | | | 0 | 10 h | 1 wk | 2 wk | 3 wk | 4 wk | 5 wk | 6 wk | 7 wk | 8 wk | 9 wk | 10 wk |
|---|---|---|---|---|---|---|---|---|---|---|---|---|---|---|
| Pre-column | pre-column used | | | | A | B | A | B | A | B | A | B | A | B |
| | presence of paraform (as determined with the naked eye) | | — | — | | | | | | | | | | |
| | reactant soln. from pre-column | Fe (ppm) | 0 | 0 | 0 | 0 | 0 | 0 | 0 | 0 | 0 | 0 | 0 | 0 |
| | | Cr (ppm) | 0 | 0 | 0 | 0 | 0 | 0 | 0 | 0 | 0 | 0 | 0 | 0 |
| | | Ni (ppm) | 0 | 0 | 0 | 0 | 0 | 0 | 0 | 0 | 0 | 0 | 0 | 0 |
| Main column | presence of paraform (as determined with the naked eye) | | — | — | | | | | | | | | | |
| | reactant soln. from main column | trioxane (wt %) | 3.2 | 3.2 | 3.2 | 3.2 | 3.2 | 3.2 | 3.2 | 3.2 | 3.2 | 3.2 | 3.2 | 3.2 |
| | | Fe (ppm) | 0 | 0 | 0 | 0 | 0 | 0 | 0 | 0 | 0 | 0 | 0 | 0 |
| | | Cr (ppm) | 0 | 0 | 0 | 0 | 0 | 0 | 0 | 0 | 0 | 0 | 0 | 0 |
| | | Ni (ppm) | 0 | 0 | 0 | 0 | 0 | 0 | 0 | 0 | 0 | 0 | 0 | 0 |
| Flow rate (cm³/h) | | | 6000 | 6000 | 6000 | 6000 | 6000 | 6000 | 6000 | 6000 | 6000 | 6000 | 6000 | 6000 |

What is claimed is:

1. A process for producing trioxane from an aqueous formaldehyde solution comprising the steps of:
    during a first stage, passing an aqueous formaldehyde solution having metallic impurities therein as a descending stream through an ion-exchange vessel containing an ion-exchange material and bringing the aqueous formaldehyde solution into contact with the ion-exchange material and thereby removing substantially the metallic impurities therefrom so as to obtain a substantially metallic impurity-free aqueous formaldehyde solution; and then subsequently
    during a second stage, passing the substantially metallic impurity-free aqueous formaldehyde solution as an ascending stream through a reaction vessel containing a solid acid catalyst so as to synthesize trioxane therefrom.

2. A process for producing trioxane according to claim 1, wherein the solid acid catalyst in the second stage is a strongly acidic cation-exchange resin.

3. A process for producing trioxane according to claim 1, wherein the second stage includes passing the substantially metallic impurity-free aqueous formaldehyde solution as an ascending stream through a column filled with the solid acid catalyst.

4. A process for producing trioxane according to claim 3, wherein the second stage includes bringing formaldehyde in said ascending stream of substantially metallic impurity-free aqueous formaldehyde solution into contact with the solid acid catalyst in the column.

5. A process for producing trioxane according to claim 1, wherein the ion-exchange material used in the first stage is a cation-exchange resin.

6. A process for producing trioxane according to claim 1, wherein the first stage includes passing the aqueous formaldehyde solution as a descending stream through two or more ion exchange material-containing columns arranged in parallel.

7. A process for producing trioxane according to claim 6, wherein the first stage includes alternately using one of the columns for removing the metallic impurities and another one of the columns for regenerating the ion-exchange material therewithin.

8. A process for producing trioxane according to claim 6, wherein the first stage includes passing the aqueous formaldehyde solution having metallic impurities therein as a descending stream through at least one of the columns.

9. A process for producing trioxane according to claim 8, wherein the first stage includes the steps of:

(i) passing the aqueous formaldehyde solution having metallic impurities therein as a descending stream through one of the columns while (ii) simultaneously passing a stream of regeneration fluid through another one of the columns.

10. The process for producing trioxane according to claim 9, wherein the stream of regeneration fluid is passed as an ascending stream through said another one of the columns.

11. The process for producing trioxane according to claim 9, wherein the first stage further includes (iii) periodically alternately switching said streams of aqueous formaldehyde solution and regeneration fluid between said one and another one of said columns.

* * * * *